United States Patent
Jones et al.

(10) Patent No.: US 10,339,767 B2
(45) Date of Patent: *Jul. 2, 2019

(54) SENSOR SYSTEMS AND METHODS FOR ANALYZING PRODUCE

(71) Applicant: Walmart Apollo, LLC, Bentonville, AR (US)

(72) Inventors: Nicholaus Adam Jones, Fayetteville, AR (US); Robert James Taylor, Rogers, AR (US); Aaron James Vasgaard, Fayetteville, AR (US); Matthew Allen Jones, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/139,424

(22) Filed: Sep. 24, 2018

(65) Prior Publication Data

US 2019/0026998 A1  Jan. 24, 2019

Related U.S. Application Data

(63) Continuation of application No. 15/697,914, filed on Sep. 7, 2017, now Pat. No. 10,083,577.

(60) Provisional application No. 62/384,791, filed on Sep. 8, 2016.

(51) Int. Cl.
| | | |
|---|---|---|
| *G07G 1/00* | (2006.01) | |
| *G01N 33/02* | (2006.01) | |
| *G06F 16/23* | (2019.01) | |
| *G06Q 10/08* | (2012.01) | |
| *G06Q 20/20* | (2012.01) | |
| *G06Q 30/02* | (2012.01) | |
| *G01N 21/3504* | (2014.01) | |
| *G06F 16/2455* | (2019.01) | |

(52) U.S. Cl.
CPC ........ *G07G 1/0009* (2013.01); *G01N 21/3504* (2013.01); *G01N 33/025* (2013.01); *G06F 16/2322* (2019.01); *G06F 16/24568* (2019.01); *G06Q 10/087* (2013.01); *G06Q 20/203* (2013.01); *G06Q 30/0201* (2013.01); *G06Q 30/0202* (2013.01)

(58) Field of Classification Search
CPC .............. G07G 1/0009; G01N 33/025; G01N 21/3504; G06Q 20/203; G06Q 10/087; G06Q 30/0201; G06Q 30/0202; G06F 17/30353

See application file for complete search history.

(56) References Cited

U.S. PATENT DOCUMENTS

| | | | |
|---|---|---|---|
| 6,069,696 | A | 5/2000 | McQueen et al. |
| 6,075,594 | A | 6/2000 | Thomas et al. |
| 6,577,983 | B1 | 6/2003 | Zhu |
| 8,113,427 | B2 | 2/2012 | Ross et al. |
| 8,874,472 | B2 | 10/2014 | Bravo |
| 9,135,491 | B2 | 9/2015 | Morandi et al. |

(Continued)

FOREIGN PATENT DOCUMENTS

WO    2006130911 A1    12/2006

*Primary Examiner* — Kristy A Haupt
(74) *Attorney, Agent, or Firm* — McCarter & English, LLP; David R. Burns; John S. Curran (57) ABSTRACT

Sensor systems, methods and machine readable medium are provided for a sensor system for analyzing the ripeness of produce items.

18 Claims, 6 Drawing Sheets

(56) References Cited

U.S. PATENT DOCUMENTS 9,659,286 B2     5/2017   Rose et al.
10,083,577 B2 *   9/2018   Jones ................ G06F 17/30516

* cited by examiner

SENSOR SYSTEMS AND METHODS FOR ANALYZING PRODUCE

RELATED APPLICATION

This application is a continuation of U.S. patent application Ser. No. 15/697,914, filed on Sep. 7, 2017, entitled "Sensor Systems and Methods for Analyzing Produce", which claims priority to U.S. Provisional Patent Application No. 62/384,791, filed Sep. 8, 2016, entitled "Sensor Systems and Methods for Analyzing Produce and Plastic Bag Properties", the contents of both of which are hereby incorporated in their entirety.

BACKGROUND

Sensors are often used to detect various data and information. Sensors can be used in various settings to make processes efficient or to increase productivity. Spectrometers can be used to obtain data relating to gases emitted by objects or data regarding light reflected by objects.

BRIEF DESCRIPTION OF THE DRAWINGS

The accompanying drawings, which are incorporated in and constitute a part of this specification, illustrate one or more embodiments of the present invention and, together with the description, help to explain the present invention. The embodiments are illustrated by way of example and should not be construed to limit the present invention. In the drawings.

DETAILED DESCRIPTION

Systems, methods, and computer readable mediums are described for a sensor system for analyzing produce. In one embodiment a sensor system includes a sensor disposed to measure gas properties emitted from, or light reflected by, produce items scanned at a computing system. The sensed data may be used to determine a customer-preferred ripeness level and to generate a report for managing inventory. In another exemplary embodiment, a sensor system includes a sensor disposed at a store exit to measure gaseous properties emitted by plastic bags to determine the number of plastic bags used by customers. This sensed data may be used as an indicator of the number of items sold during a time period and may be compared to point of sale data as a security mechanism.

Figure 1:
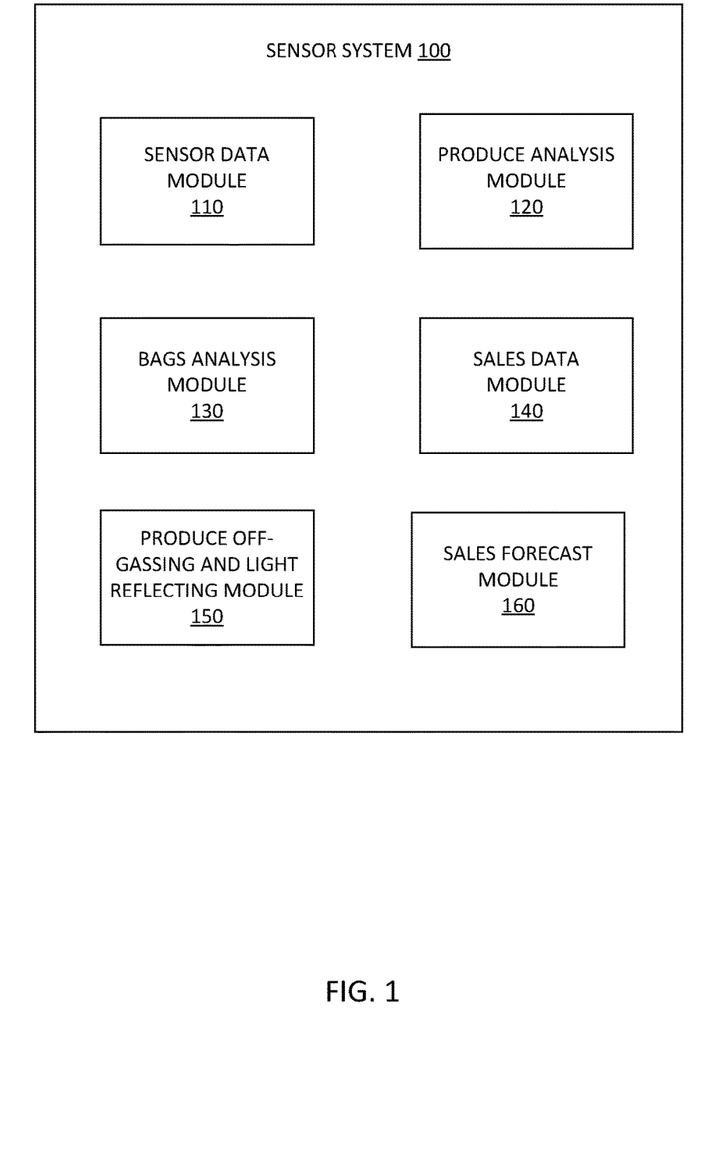
FIG. 1 is a block diagram showing an exemplary sensor system for analyzing produce, according to an example embodiment.

FIG. 1 is a block diagram showing a sensor system 100 in terms of modules for analyzing produce and plastic bags, according to an example embodiment. The one or more of the modules may be implemented in server 530 shown in FIG. 5. The modules include a sensor data module 110, a produce analysis module 120, bags analysis module 130, sales data module 140, produce off-gassing and light reflecting module 150, and sales forecast module 160. The modules may include various circuits, circuitry and one or more software components, programs, applications, or other units of code base or instructions configured to be executed by one or more processors (e.g., processors included in the server 530 shown in FIG. 5). In other embodiments, one or more of modules 110, 120, 130, 140, 150, 160 may be included in a Point-of-Sale (POS) system (e.g., POS system(s) 520 shown in FIG. 5), while other of the modules 110, 120, 130, 140, 150, 160 are provided in a server (e.g., server 530 shown in FIG. 5). Although modules 110, 120, 130, 140, 150, 160 are shown as distinct modules in FIG. 1, it should be understood that modules 110, 120, 130, 140, 150, and 160 may be implemented as fewer or more modules than illustrated. It should be understood that any of modules 110, 120, 130, 140, 150, and 160 may communicate with one or more components included in exemplary embodiments of the present disclosure (e.g., sensors 510, POS system(s) 520, server 530, or database(s) 540, 545 of system 500 shown in FIG. 5).

The sensor data module 110 may be configured to receive and manage data measured or sensed by sensors, and maintain and control the sensors. The produce analysis module 120 may be configured to store, manage and analyze the sensed data to determine a customer-preferred ripeness level for a produce item for a particular time and date. The bags analysis module 130 may be configured to store, manage and analyze the sensed data to determine a quantity of plastic bags used and calculate items per plastic bag over a period of time.

The sales data module 140 may be configured to manage and retrieve sales data from one or more POS systems and determine a quantity of items sold during a period of time. The produce off-gassing and light reflecting module 150 may be configured to manage and maintain data stored in a database, where the data indicates off-gassing and/or light reflecting properties of one or more produce items. The sales forecast module 160 may be configured to analyze sales data and customer-preferred ripeness level in order to generate a report for inventory management.

Figure 2:
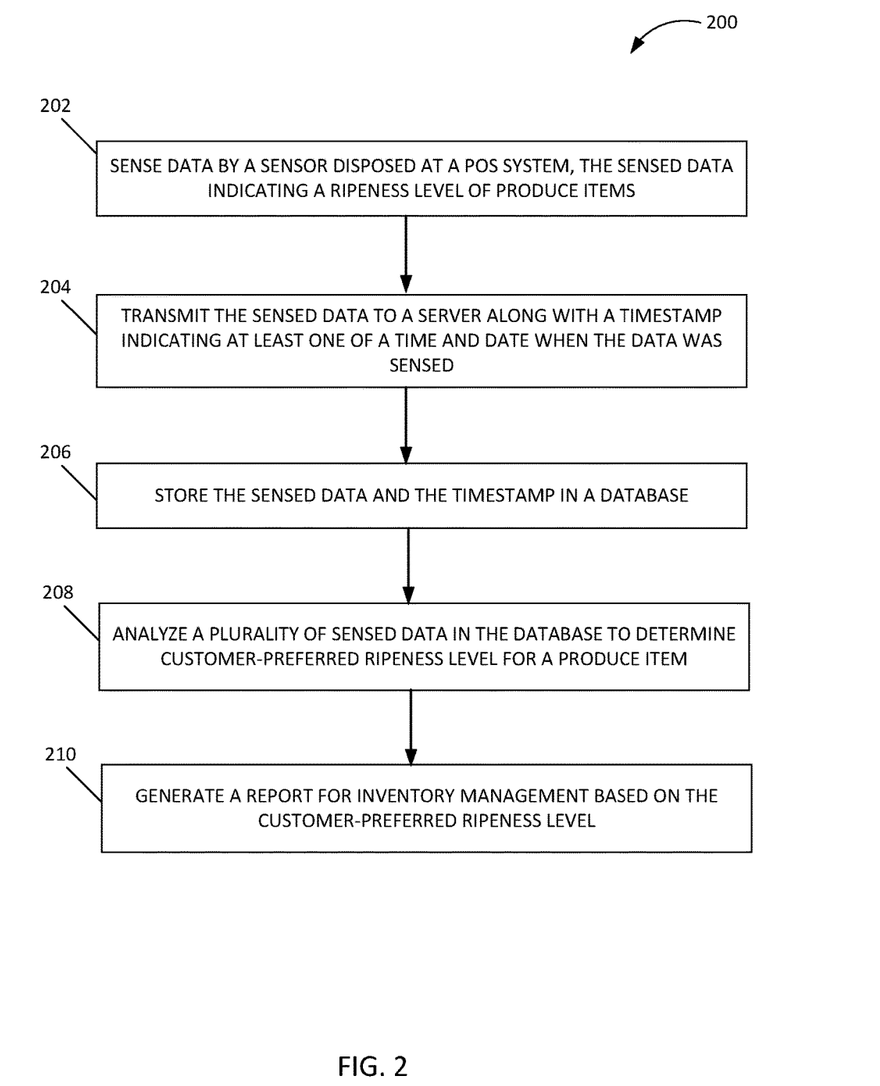
FIG. 2 is a flowchart illustrating an exemplary method for analyzing produce, according to an example embodiment.

FIG. 2 is a flowchart illustrating an exemplary method 200 for analyzing produce, according to example embodiments. The method 200 may be performed using one or more modules of the sensor system 100 described above.

At step 202, the sensor data module 110 senses data by a sensor (e.g., sensors 510) disposed at a POS system (e.g., POS system(s) 520). The sensed data may be interpreted so as to indicate a ripeness level of produce items scanned at the POS system. In an example embodiment, the sensor disposed at the POS system is a spectrometer. In some embodiments, the spectrometer measures gaseous properties emitted by a produce item (e.g., the spectrometer may measure the off gases emitted by a produce item such as a piece of fruit). In other embodiments, the spectrometer measures light reflected by a produce item (e.g., the spectrometer may identify that a piece of fruit is not reflecting as much light such as may be the case when a banana is bruised/darkened in spots). In an example embodiment, the spectrometer measures a spectrum which aides in determining the ripeness of a produce item. The sensor may be disposed at the POS system such that it senses data from the produce item when the produce item is scanned by a cashier or a customer at the POS system for purchase.

At step 204, the produce analysis module 120 transmits the sensed data to a server (e.g., server 530) along with a timestamp indicating a time and/or date when the data was sensed. In one embodiment, the produce analysis module 120 determines a stock keeping unit (SKU) number of the produce item scanned at the POS system. For example, the stock keeping unit may communicate with the POS system to identify a scanned SKU. The SKU number may be transmitted to the server with the sensed data to enable identification of the data stored for the particular produce item.

At step 206, the produce analysis module 120 stores the sensed data and timestamp in a database. In one embodiment, the produce analysis module 120 may store sensed data and timestamps for multiple produce items scanned at all of the POS systems in a store, including self-checkout POS systems.

At step 208, the produce analysis module 120 analyzes the multiple sets of sensed data that have been stored in the database to determine a customer-preferred ripeness level for a particular produce item. The multiple sets of sensed data indicate the ripeness of the produce items purchased by customers on particular times and days.

In one embodiment, the produce analysis module 120 retrieves data from a database (e.g., produce off-gassing and light reflecting database(s) 540) storing predefined criteria and data related to off-gassing and/or light reflecting properties of multiple produce items. The produce analysis module 120 compares the sensed data for a scanned produce item with an off-gassing or light reflecting property of the produce item stored in the database. Based on this comparison, the produce analysis module 120 may determine a ripeness level for the scanned produce item. In some embodiments, the ripeness level may be a discrete value (such as 1, 2, 3, 4, etc.) where a low value may indicate produce that is the least ripe and a high value may indicate produce that is the most ripe. In some embodiments, the ripeness level may be indicated on a scale (such as, low, mid-low, medium, mid-high, high, etc.). The determined ripeness level for the scanned produce item may be stored in the database.

In another embodiment, the sensed data may first be stored in the database 540 and the produce analysis module 120 may compare all of the sensed data in order to determine purchase patterns indicative of customer behavior. For example, an analysis of the sensed data may indicate that bananas may sell best before they are fully ripe while plums that are fully ripe are the most sold type of plums and peaches may continue to be popular even when they are slight past their ideal ripeness. Based on the analysis results, the produce analysis module may perform an action such as generating a report on the results or may programmatically adjust inventory orders and/or display times for the produce.

In one embodiment, the produce analysis module 120 may determine a customer-preferred ripeness level by analyzing the stored ripeness level for the scanned produce items at various times of the week. For example, the customer-preferred ripeness level may be determined based on the most recorded ripeness level for a produce item during a time period. For example, the customer-preferred ripeness level for avocados earlier in the week (Monday or Tuesday) is less ripe, while customer-preferred ripeness level for avocados later in the week (Friday or Saturday) is more ripe. Similarly, the customer-preferred ripeness level for apples may be for less ripe apples during a particular season (e.g., Fall). As another example, there may be no clear customer-preferred ripeness level for a produce item for a particular time or day. These preferences, or lack thereof, can be determined based on the purchasing habits of customers indicated by the ripeness level of produce items scanned at the POS system. In determining the customer-preferred ripeness level for a particular produce item, the produce analysis module 120 may average the recorded ripeness levels of the scanned produce items. In some embodiments, the produce analysis module 120 may normalize the recorded data for the ripeness level of the scanned produce items.

At step 210, the sales forecast module 160 generates a report for inventory management based on the customer-preferred ripeness level. The report includes information for stocking inventory based on the customer-preferred ripeness level and a time and/or date of stocking. The report may include information on which ripeness level of produce should be stocked for which time and/or day. In an example embodiment, an associate at the store checks the ripeness level of the produce items before stocking. In a non-limiting example, if there is no clear customer-preferred ripeness level for a time or day, then the report does not include any specific instructions for stocking a specific ripeness of produce.

In one embodiment, the sales forecast module 160 may generate a sales forecast for a produce item based on the customer-preferred ripeness level for a produce item over a period of time.

In an embodiment, the POS system may identify the produce item based on the off gas or light reflecting properties of the produce item, and there may be no additional need to scan the produce item for a barcode, SKU or other identifier at the POS system for a sales transaction.

Figure 3:
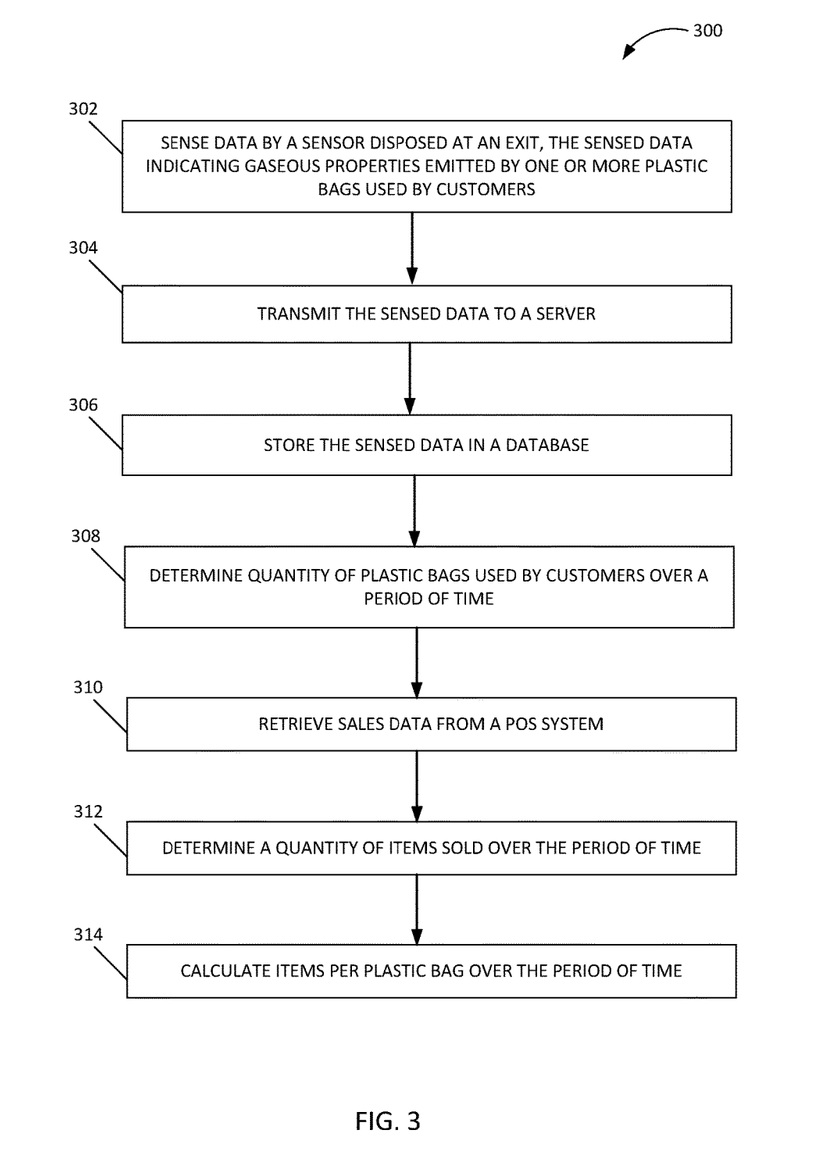
FIG. 3 is a flowchart illustrating an exemplary method for analyzing plastic bags, according to an example embodiment.

FIG. 3 is a flowchart illustrating an exemplary method 300 for analyzing plastic bags, according to example embodiments. The method 300 may be performed using or one or more modules of the sensor system 100 described above.

At step 302, the sensor data module 110 senses data by a sensor (e.g., sensors 510) disposed at an exit of the store. The sensed data indicates gaseous properties emitted by one or more plastic bags used by customers to transport purchased items. In an example embodiment, the sensor disposed at the store exit is a spectrometer. In some embodiments, the spectrometer measures gaseous properties emitted by items passing through the exit, in particular plastic bags. The sensor may be disposed at the store exit such that it senses data from the plastic bags used by customers to transport items purchased at the store.

At step 304, the sensor data module 110 transmits the sensed data to a server (e.g., server 530). At step 306, the sensor data module 110 stores the sensed data in a database (e.g., bag usage database(s) 545). The database stores multiple sets of sensed data during different time periods indicating gaseous properties emitted by the plastic bags.

At step 308, the bags analysis module 130 determines a quantity of plastic bags used by customers over a period of time based on the multiple sets of sensed data. The bag analysis module 130 may use a predefined value indicating one plastic bag to determine the quantity of plastic bags used during a period of time. The bags analysis module 130 may filter noise in the sensed data, where the noise relates to gaseous properties emitted by items other than plastic bags. In some embodiments, the bags analysis module 130 generates a notification if the bags analysis module 130 is unable to determine the quantity of plastic bags used due to noise in the multiple sets of sensed data.

At step 310, the sales data module 140 retrieves sales data from one or more POS systems. At step 312, the sales data module 140 determines a quantity of items based on the sales data sold over the period of time. In some embodiments, the sales data module 140 may differentiate between items that require bagging and items that do not require bagging. The sales data module 140 may include that information in determining the quantity of items sold.

At step 314, the bags analysis module 130 calculates the number of items per plastic bag over the period of time using the determined quantity of items sold and the determined quantity of plastic bags used.

In some embodiments, the bags analysis module 130 may detect that a shopping cart or shopping basket does not contain any plastic bags or items based on the sensed data. In this case, the bags analysis module 130 generates a security alert indicating a potential theft of the shopping cart or shopping basket. The security alert may be transmitted to store associates' devices.

The number of plastic bags used may also help determine the number of customers at a store by using sales data. The number of items sold per plastic bag may help in improving inventory management and tracking sales. For example, the sensor system 100 can correlate the number of items purchased during a time period to the number of plastic bags used to determine whether there is waste. For example, ideally one plastic bag should contain at least six items to reduce usage of plastic bags. Based on the correlation of the items purchased and the plastic bags used, the sensor system 100 can determine whether the use of plastic bags at a facility is optimal.

Figure 4:
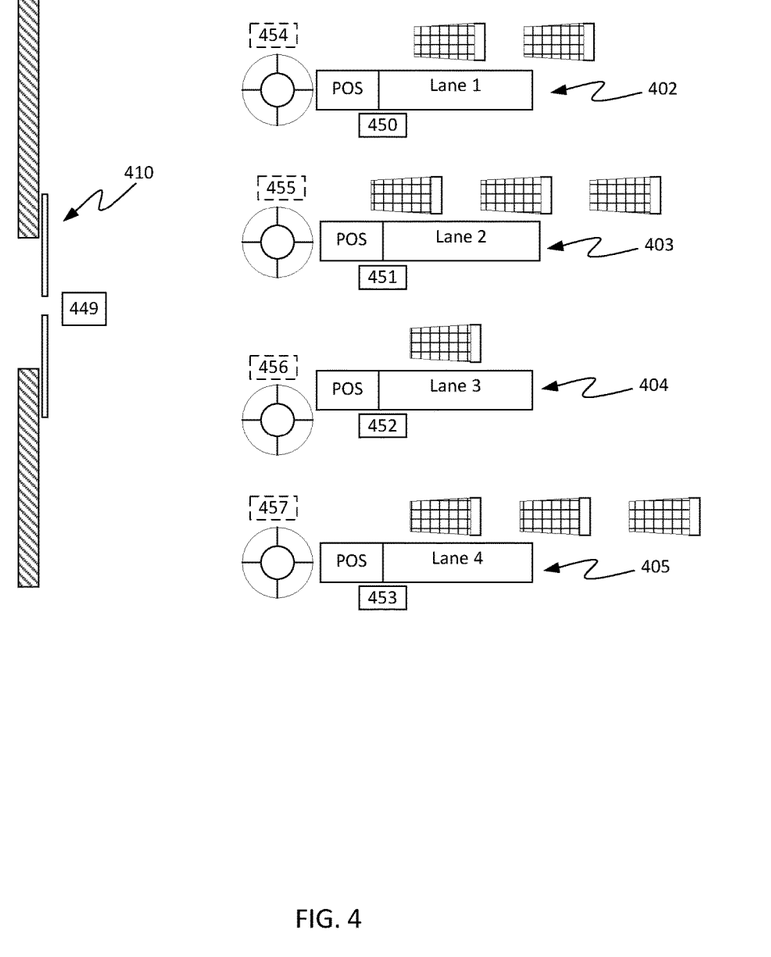
FIG. 4 schematically depicts an exemplary arrangement of sensors in a store, according to an example embodiment.

FIG. 4 schematically depicts an exemplary arrangement of sensors in a store, according to example embodiments. As shown in FIG. 4 and as described above, sensors may be disposed at the POS system, for example, as illustrated by sensors 450, 451, 452, and 453 at POS systems 402, 403, 404, and 405 respectively. Optionally, they may be disposed as illustrated by sensors 454, 455, 456, and 457. Additionally, as described above, sensors may be disposed near the store exit, for example, as illustrated by sensor 449 at store exit 410. It will be appreciated that other arrangements of sensors to detect the off-gassing and/or light reflecting properties of produce and/or plastic bags in addition to those depicted herein should also be considered to be within the scope of the present invention.

Figure 5:
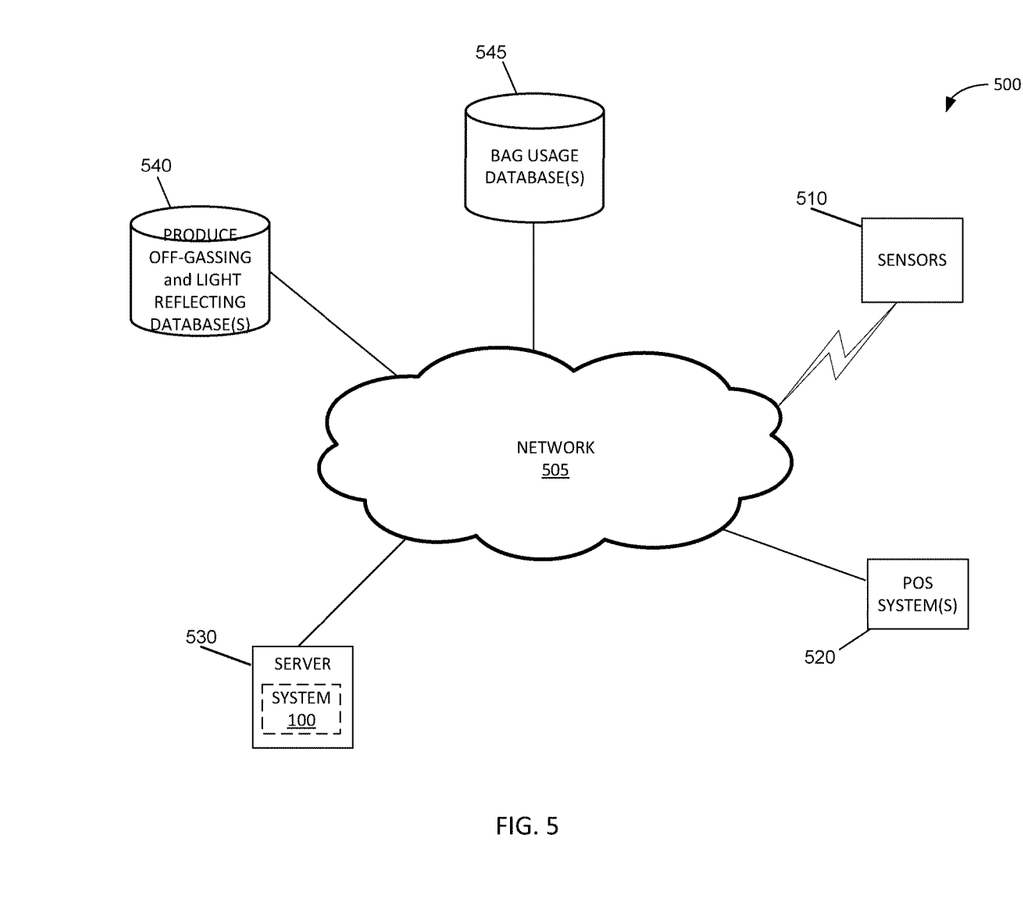
FIG. 5 is a diagram of an exemplary network environment suitable for a distributed implementation of exemplary embodiments.

FIG. 5 illustrates a network diagram depicting a system 500 for implementing the sensor system, according to an example embodiment. The system 500 can include a network 505, sensors 510, POS system(s) 520, server 530, a produce off-gassing and light reflecting database(s) 540, and a bag usage database(s) 545. Each of sensors 510, POS system(s) 520, servers 530, and database(s) 540, 545 is in communication with the network 505.

In an example embodiment, one or more portions of network 505 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

The sensors 510 may be spectrometers configured to measure gaseous properties or light reflected by items. The sensors 510 may include, but are not limited to optical spectrometers, mass spectrometer, time of flight mass spectrometer, magnetic spectrometer, and the like. The sensors 510 may connect to network 505 via a wired or wireless connection. The sensors 510 may be sensors 449-457 of FIG. 4.

The POS system(s) 520 may include, but is not limited to, cash registers, work stations, computers, general purpose computers, Internet appliances, hand-held devices, wireless devices, portable devices, wearable computers, cellular or mobile phones, portable digital assistants (PDAs), smart phones, tablets, ultrabooks, netbooks, laptops, desktops, multi-processor systems, microprocessor-based or programmable consumer electronics, network PCs, mini-computers, smartphones, tablets, netbooks, and the like. The POS system(s) 520 is part of a store infrastructure and aids in performing various transactions related to sales and other aspects of a store. Being part of a store's infrastructure, the POS system(s) 520 may be installed within the store or they may be installed or operational outside of the store. For example, the POS system(s) 520 may be a mobile device that a store employee can use outside of the store to perform transactions or other activities. In another example, the POS system(s) 520 may be a kiosk installed outside the store. Similarly, the POS system(s) 520 may be a mobile device that can be used within the store, and is not physically installed or attached to one particular location within the store. The POS system(s) 520 can include one or more components described in relation to computing device 600 shown in FIG. 6.

The POS system(s) 520 may also include various external or peripheral devices to aid in performing sales transactions and other duties. Examples of peripheral devices include, but are not limited to, barcode scanners, cash drawers, monitors, touch-screen monitors, clicking devices (e.g., mouse), input devices (e.g., keyboard), receipt printers, coupon printers, payment terminals, and the like. Examples of payment terminals include, but are not limited to, card readers, pin pads, signature pads, signature pens, Square™ registers, LevelUp™ platform, cash or change deposit devices, cash or change dispensing devices, coupon accepting devices, and the like.

The POS system(s) 520 may connect to network 505 via a wired or wireless connection. The POS system(s) 520 may include one or more applications or systems such as, but not limited to, a sales transaction application, and the like. In an example embodiment, the POS system(s) 520 may perform some of the functionalities described herein, such as scanning items for purchase. The server 530 may perform the other functionalities described herein, such as storing and analyzing sensed data, analyzing sales data, determining a customer-preferred ripeness level, and determining a quantity of items sold per plastic bag used.

Each of the database(s) 540, 545, and server 530 is connected to the network 505 via a wired connection. Alternatively, one or more of the database(s) 540, 545, and server 530 may be connected to the network 505 via a wireless connection. Server 530 may include one or more computers or processors configured to communicate with sensors 510 and/or POS system(s) 520 via network 505. Server 530 hosts one or more applications accessed by POS system(s) 520 and/or facilitates access to the content of database(s) 540, 545. Database(s) 540, 545 include one or more storage devices for storing data and/or instructions (or code) for use by server 530, and/or POS system(s) 520. Database(s) 540, 545 and server 530 may be located at one or more geographically distributed locations from each other or from POS system(s) 520. Alternatively, database(s) 540, 545 may be included within server 530.

Figure 6:
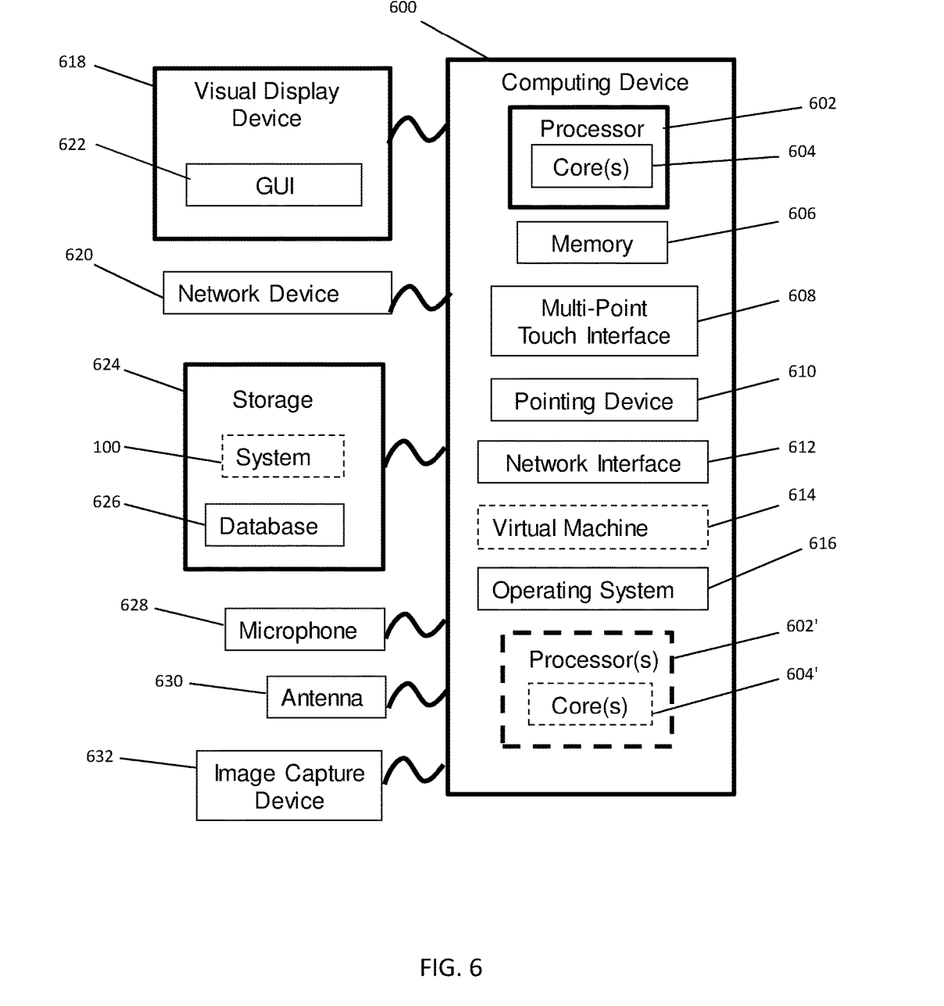
FIG. 6 is a block diagram of an exemplary computing device that may be used to implement exemplary embodiments described herein.

FIG. 6 is a block diagram of an exemplary computing device 600 that can be used to perform any of the methods provided by exemplary embodiments. The computing device 600 includes one or more non-transitory computer-readable media for storing one or more computer-executable instructions or software for implementing exemplary embodiments. The non-transitory computer-readable media can include, but are not limited to, one or more types of hardware memory, non-transitory tangible media (for example, one or more magnetic storage disks, one or more optical disks, one or more USB flashdrives), and the like. For example, memory 606 included in the computing device 600 can store computer-readable and computer-executable instructions or software for implementing exemplary embodiments. The computing device 600 also includes processor 602 and associated core 604, and optionally, one or more additional processor(s) 602' and associated core(s) 604' (for example, in the case of computer systems having multiple processors/cores), for executing computer-readable and computer-executable instructions or software stored in the memory 606 and other programs for controlling system hardware. Processor 602 and processor(s) 602' can each be a single core processor or multiple core (604 and 604') processor.

Virtualization can be employed in the computing device 600 so that infrastructure and resources in the computing device can be shared dynamically. A virtual machine 614 can be provided to handle a process running on multiple processors so that the process appears to be using only one computing resource rather than multiple computing resources. Multiple virtual machines can also be used with one processor.

Memory 606 can include a computer system memory or random access memory, such as DRAM, SRAM, EDO RAM, and the like. Memory 606 can include other types of memory as well, or combinations thereof.

A user can interact with the computing device 600 through a visual display device 618, such as a touch screen display or computer monitor, which can display one or more user interfaces 619 that can be provided in accordance with exemplary embodiments. The visual display device 618 can also display other aspects, elements and/or information or data associated with exemplary embodiments. The computing device 600 can include other I/O devices for receiving input from a user, for example, a keyboard or any suitable multi-point touch interface 608, a pointing device 610 (e.g., a pen, stylus, mouse, or trackpad). The keyboard 608 and the pointing device 610 can be coupled to the visual display device 618. The computing device 600 can include other suitable conventional I/O peripherals.

The computing device 600 can also include one or more storage devices 624, such as a hard-drive, CD-ROM, or other computer readable media, for storing data and computer-readable instructions and/or software, such as the system 100 that implements exemplary embodiments of the sensor system described herein, or portions thereof, which can be executed to generate user interface 619 on display 618. Exemplary storage device 624 can also store one or more databases for storing any suitable information required to implement exemplary embodiments. The databases can be updated by a user or automatically at any suitable time to add, delete or update one or more items in the databases. Exemplary storage device 624 can store one or more databases 626 for storing data measured by the sensors, customer-preferred ripeness level determined by system 100, quantity of items sold per plastic bag determined by system 100, and any other data/information used to implement exemplary embodiments of the systems and methods described herein.

The computing device 600 can include a network interface 612 configured to interface via one or more network devices 622 with one or more networks, for example, Local Area Network (LAN), Wide Area Network (WAN) or the Internet through a variety of connections including, but not limited to, standard telephone lines, LAN or WAN links (for example, 802.11, T1, T3, 56kb, X.25), broadband connections (for example, ISDN, Frame Relay, ATM), wireless connections, controller area network (CAN), or some combination of any or all of the above. The network interface 612 can include a built-in network adapter, network interface card, PCMCIA network card, card bus network adapter, wireless network adapter, USB network adapter, modem or any other device suitable for interfacing the computing device 600 to any type of network capable of communication and performing the operations described herein. Moreover, the computing device 600 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The computing device 600 can run operating systems 616, such as versions of the Microsoft® Windows® operating systems, different releases of the Unix and Linux operating systems, versions of the MacOS® for Macintosh computers, embedded operating systems, real-time operating systems, open source operating systems, proprietary operating systems, operating systems for mobile computing devices, or another operating system capable of running on the computing device and performing the operations described herein. In exemplary embodiments, the operating system 616 can be run in native mode or emulated mode. In an exemplary embodiment, the operating system 616 can be run on one or more cloud machine instances.

The following description is presented to enable any person skilled in the art to create and use a computer system configuration and related method and systems for a sensor system for analyzing produce and plastic bags. Various modifications to the example embodiments will be readily apparent to those skilled in the art, and the generic principles defined herein may be applied to other embodiments and applications without departing from the spirit and scope of the invention. Moreover, in the following description, numerous details are set forth for the purpose of explanation. However, one of ordinary skill in the art will realize that the invention may be practiced without the use of these specific details. In other instances, well-known structures and processes are shown in block diagram form in order not to obscure the description of the invention with unnecessary detail. Thus, the present disclosure is not intended to be limited to the embodiments shown, but is to be accorded the widest scope consistent with the principles and features disclosed herein.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components or method steps, those elements, components or steps can be replaced with a single element, component or step. Likewise, a single element, component or step can be replaced with multiple elements, components or steps that serve the same purpose. Moreover, while exemplary embodiments have been shown and described with references to particular embodiments thereof, those of ordinary skill in the art will understand that various substitutions and alterations in form and detail can be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods can include more or fewer steps than those illustrated in the exemplary flowcharts, and that the steps in the exemplary flowcharts can be performed in a different order than the order shown in the illustrative flowcharts.

What is claimed is:

1. A system for identifying and tracking ripeness levels of produce items purchased at a store to manage inventory, the system comprising:
    a server configured to execute a produce analysis module;
    a database for storing data sensed at a point-of-sale (POS) system, the database communicatively coupled with the server; and
    a sensor disposed at the POS system and in communication with the server, the sensor configured to:
        sense data measurements of a plurality of produce items scanned at the POS system,
        transmit the sensed data measurements to the server along with a timestamp indicating at least one of a time and date when the data was sensed by the sensor,
    wherein the produce analysis module is configured to:
        store the sensed data measurements and the timestamp in the database,
        analyze a plurality of sensed data measurements stored in the database taken over a period of time for a produce item, so as to determine a ripeness level from the sensed data measurements for the produce item for each timestamp stored in the database over the period of time,
        determine a customer-preferred ripeness level for the produce item for at least one of a particular time and date based on the determined ripeness level for the produce item over the period of time, and
        adjust programmatically at least one of inventory orders or display times for the produce item based on the customer-preferred ripeness level.

2. The system of claim 1, wherein the sensor measures at least one of gaseous properties emitted by the plurality of produce items, light reflected by the plurality of produce items, and a spectrum which aides in determining the ripeness of a produce item.

3. The system of claim 1, wherein the produce analysis module stores sensed data and timestamps for multiple produce items scanned at all of the POS systems in a store.

4. The system of claim 1, wherein the server is further configured to determine a SKU number based on the sensed data to identify a corresponding produce item.

5. The system of claim 1, wherein the produce analysis module is further configured to compare the sensed data to predefined criteria to determine a discrete value for the customer-preferred ripeness level.

6. The system of claim 1, wherein the produce analysis module is further configured to automatically generate a report including information on which ripeness level of produce should be stocked for which time and day.

7. A method for identifying and tracking ripeness levels of produce items purchased at a store to manage inventory, the method comprising:
    sensing data measurements of a plurality of produce items scanned at the POS system with a sensor,
    transmitting the sensed data measurements to the server along with a timestamp indicating at least one of a time and date when the data was sensed by the sensor,
    storing the sensed data measurements and the timestamp in the database,
    analyzing a plurality of sensed data measurements stored in the database taken over a period of time for a produce item, so as to determine a ripeness level from the sensed data measurements for the produce item for each timestamp stored in the database over the period of time,
    determining a customer-preferred ripeness level for the produce item for at least one of a particular time and date based on the determined ripeness level for the produce item over the period of time, and
    adjusting programmatically at least one of inventory orders or display times for the produce item based on the customer-preferred ripeness level.

8. The method of claim 7, wherein the sensing measures at least one of gaseous properties emitted by the plurality of produce items, light reflected by the plurality of produce items, and a spectrum which aides in determining the ripeness of a produce item.

9. The method of claim 7, further comprising storing sensed data and timestamps for multiple produce items scanned at all of the POS systems in a store.

10. The method of claim 7, further comprising determining a SKU number based on the sensed data to identify a corresponding produce item.

11. The method of claim 7, further comprising comparing the sensed data to predefined criteria to determine a discrete value for the customer-preferred ripeness level.

12. The method of claim 7, further comprising automatically generating a report including information on which ripeness level of produce should be stocked for which time and day.

13. A non-transitory computer readable medium storing instructions that when executed by a processor causes the processor to implement a method for identifying and tracking ripeness levels of produce items purchased at a store to manage inventory, the method comprising:
    sensing data measurements of a plurality of produce items scanned at the POS system with a sensor,
    transmitting the sensed data measurements to the server along with a timestamp indicating at least one of a time and date when the data was sensed by the sensor,
    storing the sensed data measurements and the timestamp in the database,
    analyzing a plurality of sensed data measurements stored in the database taken over a period of time for a produce item, so as to determine a ripeness level from the sensed data measurements for the produce item for each timestamp stored in the database over the period of time,
    determining a customer-preferred ripeness level for the produce item for at least one of a particular time and date based on the determined ripeness level for the produce item over the period of time, and adjusting programmatically at least one of inventory orders or display times for the produce item based on the customer-preferred ripeness level.

14. The non-transitory computer readable medium of claim 13, wherein the sensing measures at least one of gaseous properties emitted by the plurality of produce items, light reflected by the plurality of produce items, and a spectrum which aides in determining the ripeness of a produce item.

15. The non-transitory computer readable medium of claim 13, further comprising storing sensed data and timestamps for multiple produce items scanned at all of the POS systems in a store.

16. The non-transitory computer readable medium of claim 13, wherein the method further comprises determining a SKU number based on the sensed data to identify a corresponding produce item.

17. The non-transitory computer readable medium of claim 13, wherein the method further comprises comparing the sensed data to predefined criteria to determine a discrete value for the customer-preferred ripeness level.

18. The non-transitory computer readable medium of claim 13, wherein the method further comprises automatically generating a report including information on which ripeness level of produce should be stocked for which time and day.

* * * * *